United States Patent
Stassart

[11] 3,939,403
[45] Feb. 17, 1976

[54] DEVICE FOR MAINTAINING CONSTANT THE TEMPERATURE OF A COIL FED BY AN A.C. CURRENT SOURCE

[76] Inventor: Marie-Claire Stassart, rue de Londres 7, 4000 Liége, Belgium

[22] Filed: June 3, 1974

[21] Appl. No.: 476,144

[30] Foreign Application Priority Data
Apr. 11, 1974 Belgium .............. 143115

[52] U.S. Cl. .............. 324/40; 317/131; 336/179; 336/183
[51] Int. Cl.² .............. G01R 33/12; H01H 47/26
[58] Field of Search ........ 324/40, 41, 43 R; 336/55, 336/179, 183; 317/131; 328/208

[56] References Cited
UNITED STATES PATENTS

| | | | |
|---|---|---|---|
| 2,568,587 | 9/1951 | MacGeorge | 336/183 |
| 2,795,697 | 6/1957 | Nagel | 328/208 |
| 3,378,763 | 4/1968 | Hastings | 324/40 |
| 3,434,047 | 3/1969 | Brickner | 324/43 R |

FOREIGN PATENTS OR APPLICATIONS

| | | | |
|---|---|---|---|
| 575,443 | 2/1946 | United Kingdom | 324/41 |
| 155,291 | 12/1963 | U.S.S.R. | 324/40 |

*Primary Examiner*—Robert J. Corcoran
*Attorney, Agent, or Firm*—Young & Thompson

[57] ABSTRACT

A measuring coil comprises two windings, each being formed by winding simultaneously two insulated wires having the same size, the two wires of each winding extending side by side. The windings formed by the single turns of the wires in each winding are interconnected in such a way that the magnetic effects are additive in the wires of a first of said windings and subtractive in the wires of the second winding. The single turns of the first wire in each of the two windings form the measuring coil to be fed by an alternating current and the single turns of the second wire in each of said two windings form both a sensing element for measuring the temperature of the measuring coil and/or a heating element to be fed by an adjustable direct current for maintaining the coil temperature at a predetermined value with a high accuracy.

1 Claim, 2 Drawing Figures

DEVICE FOR MAINTAINING CONSTANT THE TEMPERATURE OF A COIL FED BY AN A.C. CURRENT SOURCE

This invention relates to a device which permits to maintain constant, with a high accuracy, the temperature of a measuring coil fed by a variable electrical current thereby to maintain the characteristics of said coil at the desired levels whatever the environmental conditions may be. The invention also relates to the realization of a measuring coil adapted for the temperature stabilization according to the invention.

When using coils fed by an alternating current for the purpose of making measurements on conducting materials by the Eddy current method for instance, the impedance of these coils is sensitive to the nature of the material, the distance existing between the material and the coils, and the temperature of the coils themselves.

By choosing the electrical phase angle according to which the coil impedance or the current flowing therethrough is measured, the measurement can be made independent of the coil temperature but then it is generally very sensitive to the distance between the material and the coils, and variations of said distance, due to vibrations for instance, lead to wrong measurements.

By choosing another electrical phase angle according to which the coil impedance is measured, it is also possible to make the measurement independent of variations of the distance between the material and the coils, but then the measurement is very sensitive to the coil temperature and if correct and reliable measurements are desirable, it is advisable to stabilize the coil temperature with a high accuracy.

The object of the invention is a device for permitting the temperature of a coil to be maintained constant with a high accuracy while avoiding the disadvantages of the known arrangements.

In the device according to the invention, the coil the temperature of which is to be maintained constant comprises two windings (A and B) made of two insulated and same sized wires, wound side by side and having each a first and a second end, these two windings having the same number of single turns wound in the same direction.

The second end of the first wire ($a_1$) of the first winding (A) is connected to the first end of the first wire ($a_2$) of the second winding (B), and the second end of the second wire ($b_1$) of the first winding is connected to the second end of the second wire ($b_2$) of the second winding. The first end of the first wire ($a_1$) of the first winding and the second end of the first wire ($a_2$) of the second winding are connected across an electrical alternating current source, the first end of the second wire ($b_1$) of the first winding and the first end of the second wire ($b_2$) of the second winding being connected across an adjustable electrical direct current source.

In one illustrative embodiment, the first end of the second wire ($b_1$) of the first winding and the first end of the second wire ($b_2$) of the second winding are coupled to two homologous terminals of two arms of a Wheatstone bridge network in such a way that the winding comprising the single turns of the second wire ($b_1b_2$) in said first and second windings forms an arm of the bridge network. The latter has a first crossarm including a controlled direct current generator having an input to accept a control signal for adjusting the direct current, and the two terminals of the second crossarm of the bridge network are connected to two respective inputs of a differential amplifier, the output of which is connected to the control input of said direct current generator for adjusting the generated direct current in response to the differences between the voltages at the two inputs of said differential amplifier.

The objects and features of the invention will be more clearly understood from a reading of the following description with reference to the accompanying drawings in which.

Figure 1:
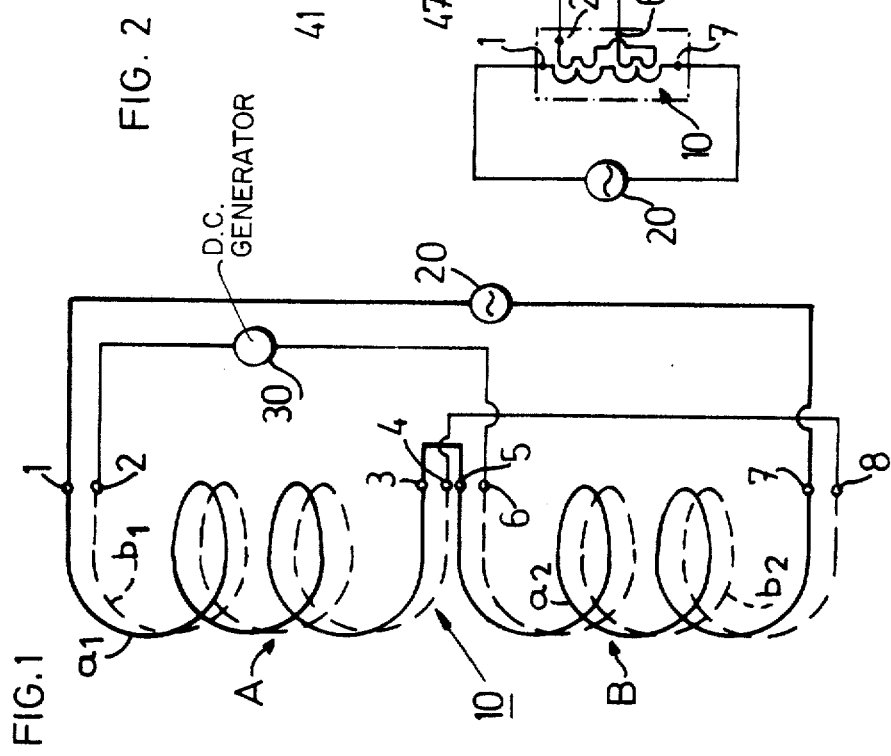
FIG. 1 is a schematic representation of the coil realization according to the invention.

According to the invention, the coil 10 the temperature of which has to be stabilized is realized as schematically shown in FIG. 1.

The coil comprises two identical windings A and B made of two insulated wires $a$ and $b$ having the same size and simultaneously wound side by side. Although the two windings A and B shown only comprise three single turns each, it is obvious that they may comprise any number of single turns.

In winding A the two wires are designated as $a_1$ and $b_1$, in winding B the two wires are designated as $a_2$ and $b_2$. The ends of the two wires $a_1$ and $b_1$ of winding A are connected to the terminals 1, 3 and 2, 4 respectively, and the ends of the two wires $a_2$ and $b_2$ of winding B are connected to the terminals 5, 7 and 6, 8 respectively.

Terminal 3 is connected to terminal 5 and terminal 4 is connected to terminal 8 so that an electrical current flowing through the single turns of wire $a$ induces a magnetic field having the same direction in the two windings A and B whereas an electrical current flowing through the single turns of wire $b$ induces a magnetic field of opposite directions in the two windings A and B.

The single turns of wire $a$ in the two windings A and B form effectively the measuring coil. The single turns of wire $b$ form both a heating element and a probe for measuring the coil temperature.

The terminals 1 and 7 are connected across an alternating current source 20 and the terminals 2 and 6 are connected across a direct current source 30. Owing to the respective directions of the single turns $a_1$, $a_2$ and $b_1$, $b_2$ in the two windings A and B, an alternating current flowing through the measuring coil $a_1a_2$ induces in the single turns $b_1$ belonging to winding A a voltage opposing to the induced voltage in the single turns $b_2$ belonging to winding B. The numbers of single turns being identical in the two windings A and B, the opposing induced voltages have the same value and the resulting voltage between the terminals 2 and 6 is substantially zero.

On the other hand, a direct current flowing through the single turns $b_1$ and $b_2$ will not affect the alternating current flowing through the single turns of the measuring coil $a_1a_2$ and this alternating current will neither be affected by the presence of any impedance which might be connected across terminals 2 and 6.

Thanks to the close coupling existing between the single turns of wire $a$ and the single turns of wire $b$ in both windings A and B as a result of the simultaneous winding of these two wires side by side, the temperature of the winding comprised of the single turns $b_1$ and $b_2$ is the same as the temperature of the measuring coil comprised of the single turns $a_1$ and $a_2$.

Figure 2:
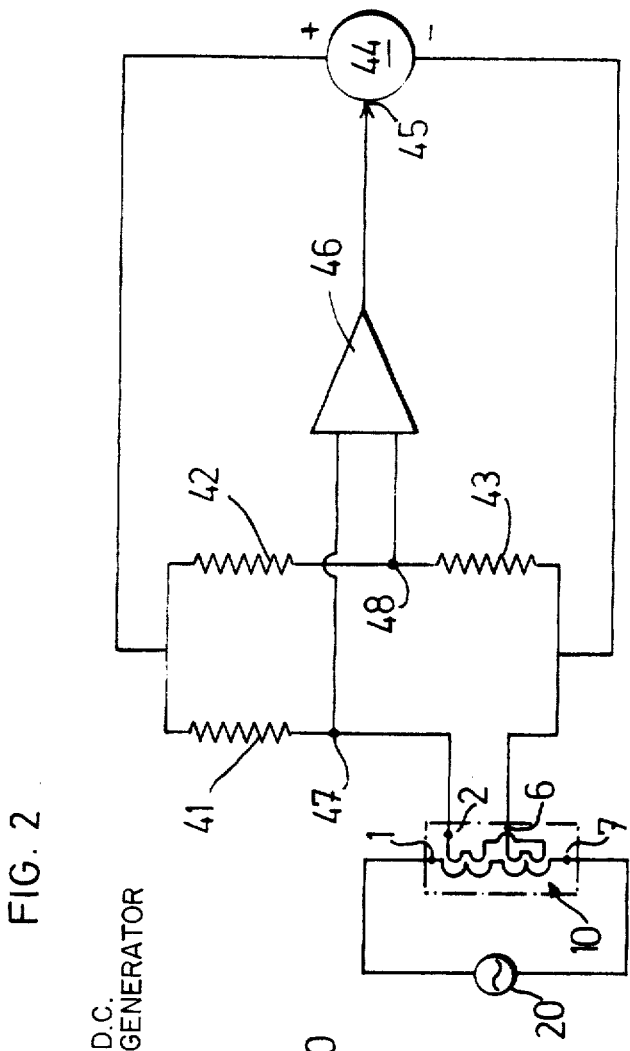
FIG. 2 is a schematic block diagram of one embodiment of the device according to the invention.

In order to maintain constant the temperature of coil 10, the latter is connected in a regulating circuit arrangement as schematically shown in FIG. 2. The arrangement comprises a Wheatstone bridge network; three arms of said network include resistors 41, 42 and 43, respectively, and the fourth arm includes the winding formed by the single turns $b_1$ and $b_2$ between the terminals 2 and 6. One crossarm of the bridge network includes a controlled direct current generator 44 adapted to be responsive to an external control signal applied to its control input 45. Said control input is coupled to the output of a differential amplifier 46 the two inputs of which are connected to the terminals 47 and 48 of the second crossarm of said bridge network. The direct current generated by the generator 44 will then be regulated in response to the voltage differences occurring between the terminals 47 and 48.

Designating the resistances of the four arms of the bridge network as $Z_b$, $Z_{41}$, $Z_{42}$ and $Z_{43}$ respectively and assuming $t_1$ is the temperature at which the coil 10 has to be maintained, then the resistance $Z_b$ of the winding $b_1 b_2$ at said temperature $t_1$ has a value $Z_{b t_1}$ given by the equation $$Z_{b t_1} = Rl/s(1 + ct_1)$$

where $R$ is the resistivity of wire $b$ $l$ is the length of wire $b$ $s$ is the cross-section of wire $b$ $c$ is the temperature coefficient of wire $b$.

If the values $Z_{41}$, $Z_{42}$ and $Z_{43}$ are chosen in such a way as to meet the equation $$\frac{Z_{41}}{Z_{b t_1}} = \frac{Z_{42}}{Z_{43}},$$

then the voltage difference between the terminals 47 and 48 will be substantially zero when the coil 10 is at the required temperature $t_1$. For any temperature deviation relative to $t_1$, a voltage difference will appear between the terminals 47 and 48 and a signal will appear then at the output of differential amplifier 46. This signal causes the direct current produced by the generator 44 to be adjusted so as to reduce the sensed temperature deviation to zero. If the differential amplifier 46 has a sufficient gain, the temperature $t_1$ can be maintained with a high accuracy.

The current flowing through wire $b$ causes heating of the latter by Joule effect. The resistors 41 to 43 also get heated by the current flow, but when taking care to limit said heatings by a suitable choice of the resistor values and/or by choosing resistors having a very small temperature coeffeicient, the values $Z_{41}$ to $Z_{43}$ will remain substantially constant whatever the ambiant conditions may be.

The regulating circuit should have a sufficient time constant to avoid too rapid variations of the direct current produced by the generator 44 to occur inasmuch such rapid variations of the current in wire $b$ would induce extraneous voltages in wire $a$.

It is to be understood that the embodiment shown is just an example serving to illustrate the principles of the invention and that many variations can be made by one skilled in the art without departing from the scope of the invention.

What is claimed is:

1. In a device for maintaining constant the temperature of a coil fed by an electrical alternating current source, said coil comprising two windings (A and B), each of said windings being formed by winding simultaneously two insulated wires ($a_1$, $b_1$ and $a_2$, $b_2$ respectively) having the same size, said two wires of each winding extending side by side and having each a first and a second end, said two windings having the same number of single turns wound in the same direction, means connecting the second end of the first wire ($a_1$) of the first winding (A) to the first end of the first wire ($a_2$) of the second winding (B), means connecting the second end of the second wire ($b_1$) of the first winding to the second end of the second wire ($b_2$) of the second winding, and means connecting the first end of the first wire ($a_1$) of the first winding and the second end of the first wire ($a_2$) of the second winding across said electrical alternating current source, the improvement comprising:

a. a Wheatstone bridge comprising four arms, the first end of the second wire ($b_1$) of the first winding (A), and the first end of the second wire ($b_2$) of the second winding (B) being connected into the bridge to form one leg thereof, the other three legs consisting of resistors, such that said second wires are traversed by an electric current in opposite directions and that the resistances of said second wires ($b_1$, $b_2$) are balanced by said resistors, b. a differential amplifier having two inputs, said inputs being connected to the end terminals of a first crossarm of said bridge, and c. a voltage-controlled direct source having two terminals and a control input, said two terminals being connected to the end terminals of the second crossarm of said bridge and said control input being connected to the output of said differential amplifier.

* * * * *